United States Patent
Mainwaring et al.

(10) Patent No.: US 11,351,249 B2
(45) Date of Patent: Jun. 7, 2022

(54) VACCINE COMPOSITIONS COMPRISING A WATER-IN-OIL EMULSION, IMMUNOGEN-LOADED HYDROGEL PARTICLES, AND CATIONIC POLYMER

(71) Applicant: CAPSULAR TECHNOLOGIES PTY LTD, Hawthorn (AU)

(72) Inventors: David E. Mainwaring, Princes Hill (AU); Mohammad Al Kobaisi, Balwyn (AU)

(73) Assignee: CAPSULAR TECHNOLOGIES PTY LTD, Hawthorn (AU)

(*) Notice: Subject to any disclaimer, the term of this patent is extended or adjusted under 35 U.S.C. 154(b) by 0 days.

(21) Appl. No.: 16/979,780

(22) PCT Filed: Mar. 13, 2019

(86) PCT No.: PCT/AU2019/050225
§ 371 (c)(1),
(2) Date: Sep. 10, 2020

(87) PCT Pub. No.: WO2019/173971
PCT Pub. Date: Sep. 19, 2019

(65) Prior Publication Data
US 2021/0038714 A1 Feb. 11, 2021

(30) Foreign Application Priority Data

Mar. 13, 2018 (AU) .................. 2018900822

(51) Int. Cl.
*A61K 39/39* (2006.01)
*A61K 9/00* (2006.01)
*A61K 39/12* (2006.01)
*A61K 39/00* (2006.01)

(52) U.S. Cl.
CPC ............ *A61K 39/39* (2013.01); *A61K 9/0019* (2013.01); *A61K 39/12* (2013.01); *A61K 2039/55566* (2013.01); *A61K 2039/55583* (2013.01)

(58) Field of Classification Search
None
See application file for complete search history.

(56) References Cited

U.S. PATENT DOCUMENTS

| | | | | |
|---|---|---|---|---|
| 5,529,777 | A * | 6/1996 | Andrianov | A61K 39/39 |
| | | | | 424/184.1 |
| 2010/0150960 | A1 * | 6/2010 | Schlom | A61K 39/292 |
| | | | | 424/208.1 |

OTHER PUBLICATIONS

Zarate et al. (Journal of Microencapsulation. 2011; 28 (7): 614-620).*
Hirata et al. (Journal of Immunology. 1966; 96 (4): 611-613).*
Derwent absract of CN 106701730 by Lou et al. May 2017.*
Carroll, E.C. et al. (Mar. 15, 2016). "The Vaccine Adjuvant Chitosan Promotes Cellular Immuity via DNA Sensor cGAS-STING-Dependent Induction of Type I Interferons," Immunity 44:597-608.

(Continued)

*Primary Examiner* — Shanon A. Foley
(74) *Attorney, Agent, or Firm* — Morrison & Foerster LLP

(57) ABSTRACT

The invention relates generally to vaccine compositions that are capable of eliciting and sustaining an immune response in a subject. The vaccine composition comprises a water-in-oil emulsion and a plurality of immunogen loaded hydrogel particles surrounded with a cationic polymer shell dispersed in the aqueous phase of the emulsion.

21 Claims, 5 Drawing Sheets

(56) References Cited

OTHER PUBLICATIONS

International Preliminary Report on Patentability dated Sep. 15, 2020, for PCT Application No. PCT/AU2019/050225, filed on Mar. 13, 2019, 5 pages.
International Search Report and Written Opinion dated Apr. 16, 2019, for PCT Application No. PCT/AU2019/050225, filed on Mar. 13, 2019, 7 pages.
Jiang, G.E. et al. (2001). "Evaluation of Alginate Microspheres Prepared by Emulsion and Spray Methods for Oral Vaccine Delivery Systems," J. Kor. Pharm. Sci. 31(4):241-256. (Translation of the Abstract Only.).
Jin, Z. et al. (Sep. 1, 2017). "Response of Live Newcastle Disease Virus Encapsulated in N-2-Hydroxpropyl Dimethylethyl Ammonium Chloride Chitosan Nanoparticles," Carbohydrate Polymers 171:267-280.
Kalaivani, M. et al. (Apr.-Jun. 2010). "Preparation and Characterisation of Alginate Coated Chitosan Microspheres for Bacterial Vaccines," Research J. Pharm. And Tech. 3(2):503-506.
Liau, J.J. et al. (2016). "Development of a Multi-Compartmental Oral Vaccine Delivery System," Drug Delivery Letters 6:57-62.
Mohamed, S.H. et al. (Jan. 2018, e-pub. Feb. 9, 2017). "Preparation and Immunological Evaluation of Inactivated Avian Influenza Virus Vaccine Encapsulated in Chitosan Nanoparticles," Biologicals 51:46-53.
Neamtu, I. et al. (2017, e-pub. Feb. 9, 2017). "Basic Concepts and Recent Advances in Nanogels as Carriers for Medical Applications," Drug Delivery 24:539-557.
Peek, L.J. et al. (2008, e-pub. Feb. 7, 2008). "Nanotechnology in Vaccine Delivery," Advanced Drug Delivery Reviews 60:915-928.
Qaqish, R. et al. (Feb. 1999). "Synthesis of a Fluorescent Chitosan Derivative and Its Application for the Study of Chitosan-Mucin," Carbohydrate Polymers 38:99-107.
Saravanakumar, A. et al. (2011). "Development, Characterization, and in Vitro Evaluation of Chitosan and Alginate Microspheres Loaded Tetanus Toxoid Vaccine: A Comparative Study," International Journal of Green Nanotechnology 3:83-91.
Wang, Y-Q. et al. (Oct. 2016). "The Potential Adjuvanticity of Quaternized Chitosan Hydrogel Based Microparticles for Porcine Reproductive and Respiratory Syndrome Virus Inactivated Vaccine," International Immunopharmacology 39:84-91.

* cited by examiner

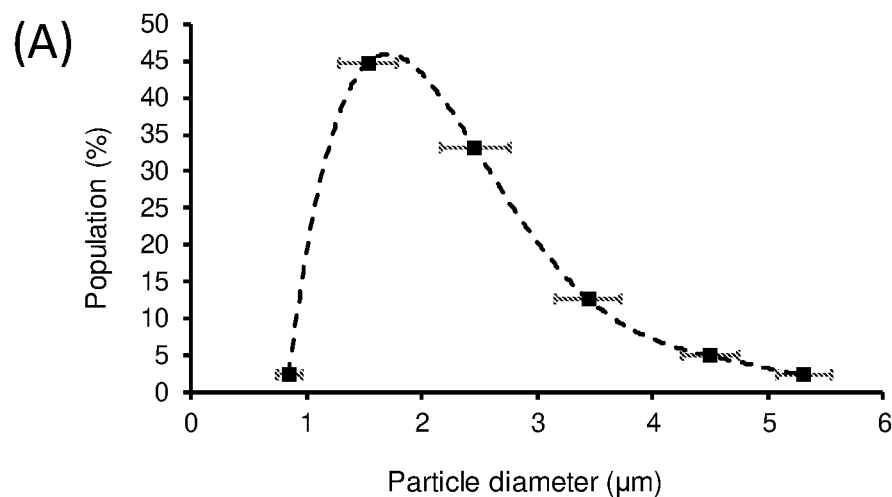
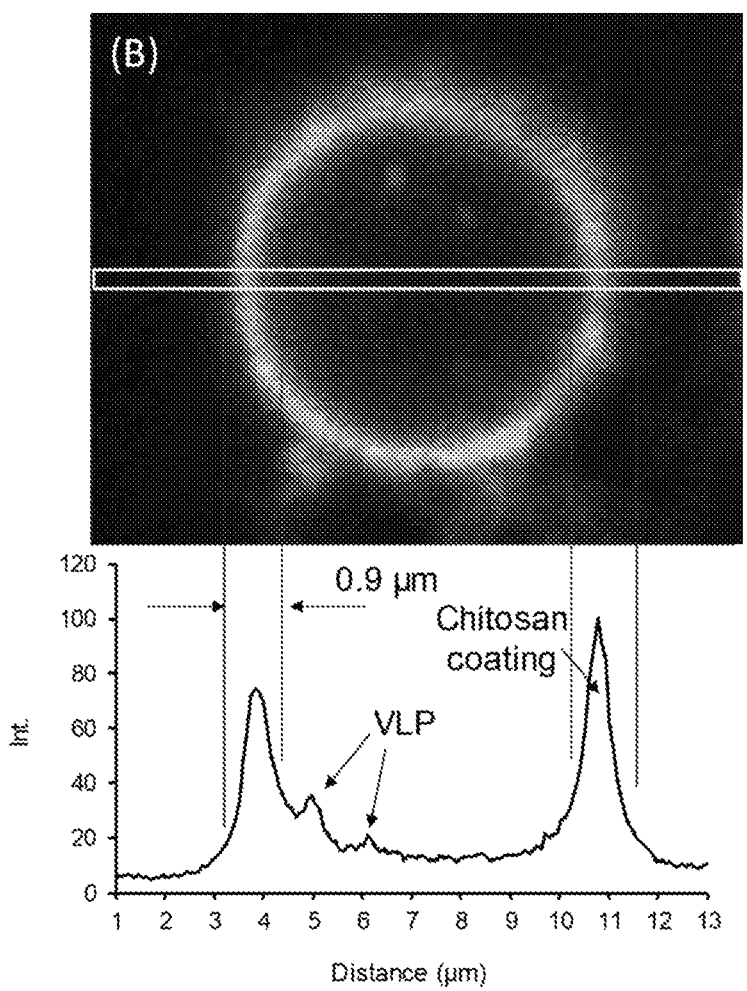
Figure 1 (A&B)

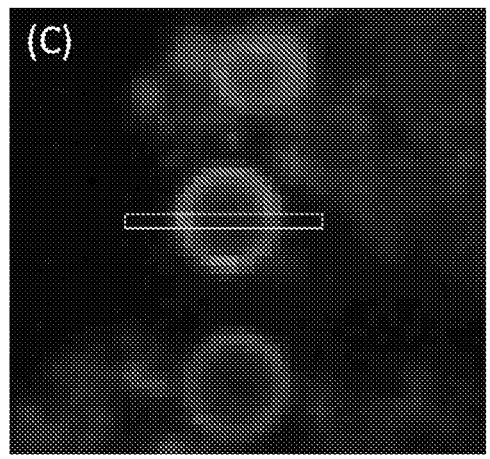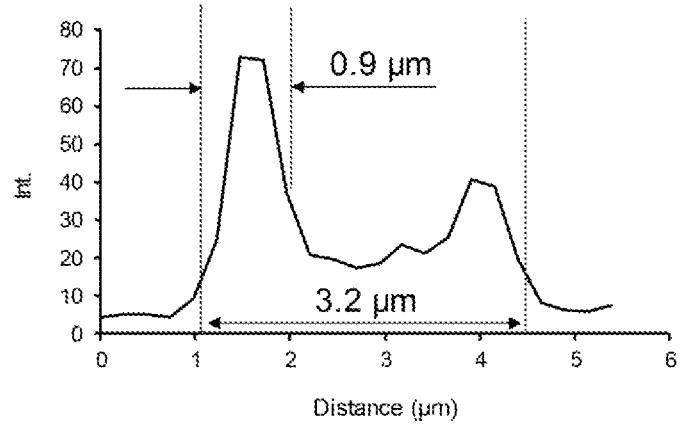
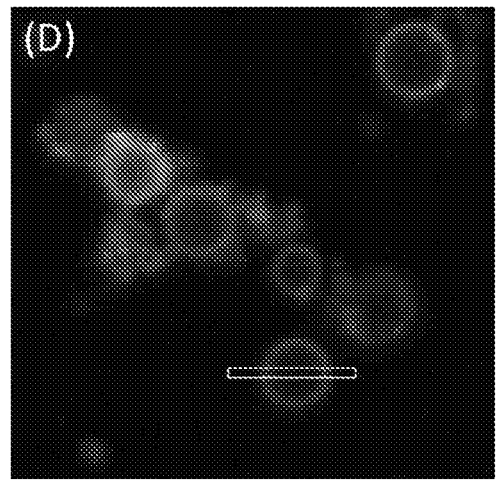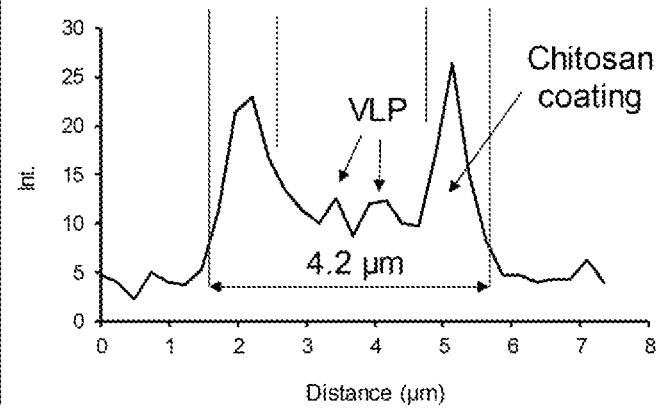
Figure 1 (C&D)

VACCINE COMPOSITIONS COMPRISING A WATER-IN-OIL EMULSION, IMMUNOGEN-LOADED HYDROGEL PARTICLES, AND CATIONIC POLYMER

CROSS REFERENCE TO RELATED APPLICATIONS

This application is a national stage application under 35 U.S.C. § 371 of International Application No. PCT/AU2019/050225, filed internationally on Mar. 13, 2019, which claims priority to Australian Patent Application No. 2018900822, filed on Mar. 13, 2018, each of which is hereby incorporated by reference in its entirety.

TECHNICAL FIELD

The present invention relates generally to vaccine compositions that are capable of eliciting and sustaining an immune response in a subject.

BACKGROUND

Vaccines have an important role to play in the prevention and control of infectious diseases. However, a disadvantage of many conventional vaccine formulations is their need to be administered in multiple vaccinations in order to provide effective immunity. If one or more of the multiple vaccinations is delayed or omitted, this may result in a failure to achieve effective protection against a disease pathogen.

There is a growing interest in the delivery of particulate vaccines for both human and animal heath, such as for instance, loaded virus like particles (VLP), pathogen mimicking particles, and killed and attenuated bacterial vaccines. Carroll et al (Carroll et al., 2016, Immunity, 44, 597-608) have shown that chitosan promotes dendritic cell maturation, where they show co-injection of chitosan enhanced the specific immunoglobulin (IgG) and antibody responses. Here, chitosan induced DC maturation without secretion of pro-inflammatory cytokines while triggering innate and adaptive immune responses. Nanogel particles are frequently used to deliver a wide spectrum of therapeutic agents particularly drugs (Neamtu et al., 2017, Drug Delivery, 24, 539-557). Peek et al. (Peek et al., 2008, Advanced Drug Delivery Reviews, 60, 915-928) reviewed clinical results of various nanoscale delivery systems in the presence of adjuvants such as the Montanides including oral delivery of virus-like particles (VLPs). Here VLPs have been reported to stimulate both cellular and humoral immunity. Avian influenza virus vaccine in chitosan nanoparticles, when in the presence of oil-emulsion adjuvant, has been shown to be more effective since it provides both humoral immunity and cellular immunity unlike conventional formulations (Mohamed et al., 2018, Biologicals, 51, 46-53). Wang et al. (Wang et al., 2016, International Immunopharmacology, 39, 84-9) showed that pH sensitive chitosan gel microparticles loaded with inactivated porcine reproductive and respiratory virus, when intramuscularly injected, elicited significantly higher cell-mediated immune responses than Montanide ISA206. Functionalised chitosan microparticles containing attenuated live Newcastle disease virus provided a safe and efficient delivery for mucosal immunity (Jin et al., 2017, Carbohydrate Polymers, 171, 267-280)

The material properties of particulate systems for therapeutic delivery (drugs and vaccines) have been widely studied and reviewed in terms of particle size, shape, and surface composition. For instance, studies have been conducted which investigate the role of PEG particle elasticity on blood circulation, cellular phagocytosis and endocytosis as well as targeting following intravenous injection. Reports show that low Young modulus acrylamide-methacrylate particles were significantly more internalised in macrophage cells compared to their stiffer counterparts. The emphasis has largely been on nanoparticles having diameters less than about 200 nm.

Immuno-responsive particles in the micrometer range can also be taken up by phagocytic antigen-presenting cells such as macrophages and dendritic cells where they showed that polyacrylamide particles of diameters up to 3.5 µm containing a protein antigen were taken up activating T-cell response. While these studies suggest an important role of particulate systems for therapeutic delivery the fact remains that when delivering particulate immunogens in a particulate vaccine composition system it is important to have the particulates properly solubilised in order to avoid or minimise any unwanted immune response and to elicit the required immune response over the required duration.

There remains a need to develop vaccine compositions and preferably vaccine compositions for particulate immunogens, that at least ameliorate one or more disadvantages associated with existing vaccine compositions and which can elicit an effective (i.e., priming) and sustained immune response in a subject.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

The present invention provides a vaccine composition for eliciting an effective and sustained immune response in a subject, such as a livestock animal.

Without wishing to be bound by theory the present inventors have engineered injectable particulate immunogen containing vaccine compositions that provide an effective primary dose and persistent (or sustained) dose in a single formulation. This has been achieved by a formulation consisting of a water in oil emulsion wherein dispersed in the aqueous phase is a specifically designed biopolymer microhydrogel network consisting of an inner depot core of physically crosslinked hydrogel particles encapsulated by a crosslinked biocompatible cationic polymer membrane of opposite charge. It is postulated that the biocompatible cationic polymer membrane advantageously enhances the immuno-activity of the microhydrogel structure due to its immunogenic properties. The particulate immunogens, such as antigen vaccines may be exemplified by virus-like particle (VLPs).

In certain embodiments the aqueous micro-hydrogel in adjuvant oil emulsion provides an initial depot effect. The size and elasticity of the capsular micro-hydrogel particles induce transport from the injection site through the lymphatic system to the lymph nodes. Control of antigen presentation and longevity of the immune-response is gained through the partition of, for instance, VLPs between the hydrogel particle (core) and the encapsulating biocompatible cationic polymer membrane (such as a chitosan membrane).

In the above embodiment the primary inoculation dose (or priming dose)—upon injection—is provided by VLPs of the encapsulating biocompatible cationic polymer following the uptake of the micro-hydrogel particles by dendritic cells and macrophages of the lymph nodes brought about by dissolution in the pH of the cellular lysosomes (~5.5). The remaining VLPs in the core hydrogel particle are subsequently released by slower enzymatic biopolymer degradation in the acidic lysosome of these cells. The present inventors have, for the first time, identified that the relative extent of the primary dose and the sustained release can be controlled by relative rates of these two mechanisms and the thickness of the VLP containing biocompatible cationic. Additionally, the inventors have found that the integrity of the VLPs are maintained by the charge neutralizing or cationic coating through the use of charge interactions or electrostatic interactions (such as charge neutralizing interaction with the anionic core biopolymer; see for instance, FIG. 6). This provides a two-fold advantage to the vaccine composition. Control of the thickness of this VLP containing outer coating (charge neutralizing zone) prevents the degradation and/or deactivation of the VLPs at least in the core before they reach the site of interest and also allows for the release of VLPs in the cationic polymer as a primary dose. Longer term secondary persistent immunization is then brought about by the slower enzymatic degradation of the hydrogel core (e.g., alginate core) depot providing release of the remaining VLPs. This system design provides a hierarchy of kinetic control mechanisms to provide controlled release and prolonged immunological responses. Thus, in relation to this advantageous embodiment of the invention, a portion of the immunogen (eg VPLs) is partitioned within the hydrogel particles to provide for a persistent dose and a portion of the immunogen is partitioned within the biocompatible cationic polymer attached to the hydrogel particles (e.g., as a continuous or non-continuous shell that surrounds the hydrogel particles) to provide for an initial immediate priming dose.

In one aspect, the present invention provides vaccine composition comprising:
a water-in-oil emulsion;
a plurality of hydrogel particles loaded with an immunogen dispersed in the aqueous phase of the water-in-oil emulsion, and
a biocompatible cationic polymer attached to the hydrogel particles.

In another aspect, the present invention provides a vaccine composition comprising:
a water-in-oil emulsion;
a plurality of alginate particles loaded with a particulate immunogen dispersed in the aqueous phase of the water-in-oil emulsion, and
chitosan surrounding and complexed with the alginate particles.

In another aspect, the present invention provides a vaccine composition comprising:
a water-in-oil emulsion;
a plurality of alginate particles loaded with virus-like particles (VLP) dispersed in the aqueous phase of the water-in-oil emulsion, and
chitosan surrounding and complexed with the alginate particles.

In another aspect, the present invention provides vaccine composition comprising:
a water-in-oil emulsion;
a plurality of hydrogel particles loaded with an immunogen dispersed in the aqueous phase of the water-in-oil emulsion, and
a biocompatible cationic polymer attached to the hydrogel particles, wherein substantially all of the immunogen is sequestered in the hydrogel particles and/or in the biocompatible cationic polymer.

In another aspect, the present invention provides a vaccine composition comprising:
a water-in-oil emulsion;
a plurality of alginate particles loaded with a particulate immunogen dispersed in the aqueous phase of the water-in-oil emulsion, and
chitosan surrounding and complexed with the alginate particles, wherein substantially all of the immunogen is sequestered in the hydrogel particles and/or in the biocompatible cationic polymer.

In another aspect, the present invention provides a vaccine composition comprising:
a water-in-oil emulsion;
a plurality of alginate particles loaded with virus-like particles (VLP) dispersed in the aqueous phase of the water-in-oil emulsion, and
chitosan surrounding and complexed with the alginate particles, wherein substantially all of the immunogen is sequestered in the hydrogel particles and/or in the biocompatible cationic polymer.

The present invention also provides a method of delivering an immunogen, and more preferably a particulate immunogen, to a subject for the treatment or prevention of a disease or disorder in the subject, the method comprising the step of administering the vaccine composition of any one of the embodiments described to the subject by injection.

The present invention also provides for use of a vaccine composition of any one of the embodiments described herein in the manufacture of a medicament for the treatment or prevention of a disease or disorder in a subject.

The vaccine composition may suitably be administered to a subject for delivery of a virus-like particle (VLP) or any other antigen that is not readily soluble in the aqueous phase, to elicit an immune response.

Further aspects appear below in the detailed description.

BRIEF DESCRIPTION OF THE FIGURES

Embodiments of the invention will now be described with reference to the following non-limiting figures in which:

FIG. 1 shows (A) a graph illustrating the particle size distribution of virus-like particle (VLP) loaded alginate microhydrogels surrounded by a continuous shell containing chitosan in a vaccine composition of one embodiment of the invention, and (B)-(D) images and graphs showing the microstructure of alginate microhydrogels loaded with baculovirus as a model for virus-like particles (VLP) with a continuous chitosan-containing coating in an emulsion containing Montanide™ ISA 201 VG (a common adjuvant for foot and mouth disease (FMD) viral vaccines, which shows rapid cellular immune response post-vaccination).

DETAILED DESCRIPTION

Figure 2:
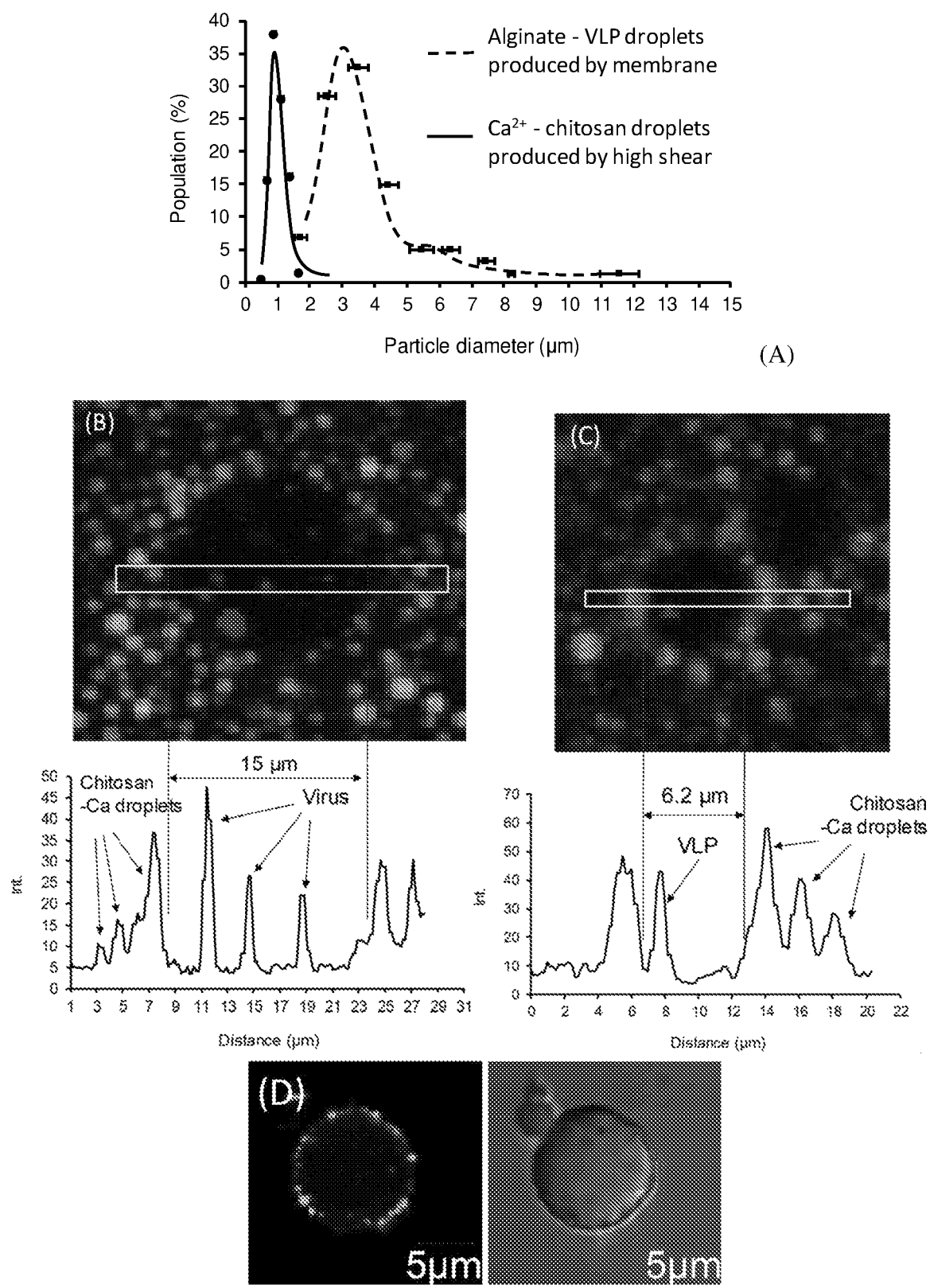
FIG. 2 shows (A) a graph illustrating the particle size distribution of virus-like particle (VLP) loaded alginate microhydrogels and chitosan-containing droplets surrounding the microhydrogels in a vaccine composition of one embodiment of the invention, (B)-(C) images and graphs showing the microstructure of VLP loaded alginate microhydrogels surrounded by chitosan-containing droplets in an emulsion containing Montanide™ ISA 61VG, and (D) images of the alginate microhydrogels loaded with VLP surrounded by a contiguous chitosan coating on the surface.
Figure 3:
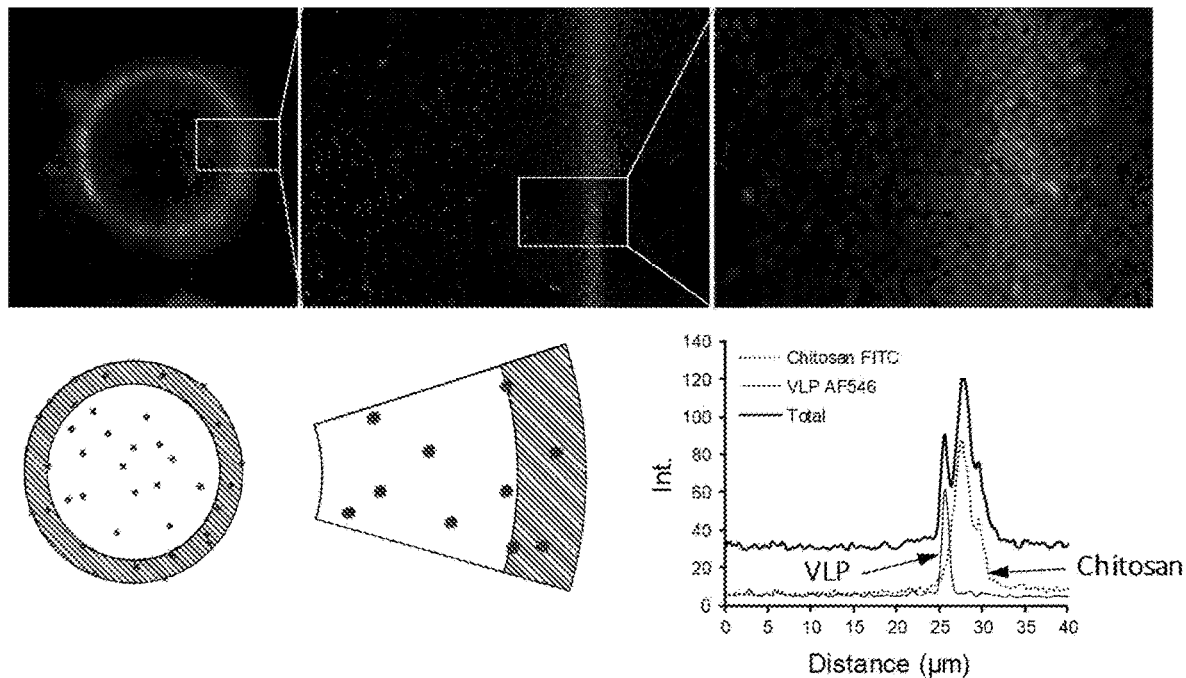
FIG. 3 shows the distribution of VLPs between the inner alginate core and the encapsulating chitosan membrane of the aqueous microhydrogel particles as both microscopy images and diagrammatic images. The presence of VLPs within the chitosan membrane is shown by the radial intensity profile of differentially labelled VLPs (Alexa Fluor 546 labelled) and chitosan (FITC labelled).

The present invention relates to vaccine compositions that are capable of eliciting a desired immune response in a subject.

In another aspect the present invention provides a vaccine composition comprising:
a water-in-oil emulsion;
a plurality of hydrogel particles loaded with an immunogen dispersed in the aqueous phase of the water-in-oil emulsion, and
a biocompatible cationic polymer attached to the hydrogel particles,
wherein a portion of the immunogen is partitioned within the hydrogel particles to provide for a persistent dose and a portion of the immunogen is partitioned within the biocompatible cationic polymer attached to the hydrogel particles to provide for an initial priming dose.

The aforementioned partitioning is such that substantially all of the immunogen is sequestered in the hydrogel particles and/or in the biocompatible cationic polymer. Accordingly, the main advantage of the present invention is the ability to effectively deliver non-aqueous soluble immunogens such as certain particulate immunogens.

In this context it will be appreciated that "substantially all" means that almost none of the immunogen is present in the bulk aqueous phase of the emulsion. That is, for instance, >95% of the immunogen is sequestered in the hydrogel particles and/or in the biocompatible cationic polymer.

The vaccine composition of the invention comprises a water-in-oil (W/O) emulsion. A skilled person would understand that a water-in-oil emulsion comprises an oil phase and an aqueous phase dispersed in the oil phase. The oil phase may form a continuous phase of the emulsion while the aqueous phase forms the dispersed phase.

The vaccine composition also comprises a plurality of hydrogel particles, which are loaded with an immunogen. The immunogen loaded hydrogel particles are dispersed in the aqueous phase of the water-in-oil emulsion.

The term "hydrogel particles" as used herein refers to discrete colloidal portions of hydrogel material. A skilled person would understand that hydrogel materials are hydrophilic polymeric materials swollen or hydrated by an aqueous liquid to be in a gel state.

The hydrogel particles of the vaccine composition described herein will generally be low modulus, soft materials comprising a low solids content and high water content. In some embodiments, the hydrogel particles may have a Young's modulus in the range of from about 5 to 700 kPa, for instance 10 kPa, or 20 kPa, or 30 kPa, or 40 kPa, or 50 kPa, or 60 kPa, or 70 kPa, or 80 kPa, or 90 kPa, or 100 kPa, or 110 kPa, or 120 kPa, or 130 kPa, or 140 kPa, or 150 kPa, or 160 kPa, or 170 kPa, or 180 kPa, or 190 kPa, or 200 kPa, or 210 kPa, or 220 kPa, or 230 kPa, or 240 kPa, or 250 kPa, or 260 kPa, or 270 kPa, or 280 kPa, or 290 kPa, or 300 kPa, or 310 kPa, 320 kPa, or 330 kPa, or 340 kPa, or 350 kPa, or 360 kPa, or 370 kPa, or 380 kPa, or 390 kPa, or 400 kPa, or 410 kPa, or 420 kPa, or 430 kPa, or 440 kPa, or 450 kPa, or 460 kPa, or 470 kPa, or 480 kPa, or 490 kPa, or 500 kPa, or 510 kPa, or 520 kPa, or 530 kPa, or 540 kPa, or 550 kPa, or 560 kPa, or 570 kPa, or 580 kPa, or 590 kPa, or 600 kPa, or 610 kPa, or 620 kPa, or 630 kPa, or 640 kPa, or 650 kPa, or 660 kPa, or 670 kPa, or 680 kPa, or 690 kPa, or any range that can be formed based on the above. The hydrogel particles may further have a water content of at least 40%, for instance, at least 45%, at least, at least 50%, at least 55%, at least 60%, at least 65%, at least 70%, at least 75% or at least 80%. In some embodiments, the water content is preferably at least 80%.

In some embodiments, the hydrogel particles may be in the form of microhydrogels. The term "microhydrogels" is used herein as a reference to discrete portions of hydrogel having dimensions (e.g. a particle diameter) in the nanometer (nm) to micrometer (µm) range. Such microhydrogels may be nanometer or micrometer sized droplets comprising or composed of hydrated polymer gel.

In some embodiments, the hydrogel particles can be colloidal portions of hydrogel material having a diameter in the range of from about 500 nm to 20 µm, preferably from about 1 µm to about 10 µm, for instance, about 1 µm, 2 µm, 3 µm, 4 µm, 5 µm, 6 µm, 7 µm, 8 µm, 9 µm, to about 10 µm, and ranges within. Hydrogel particles according to such embodiments may be referred to herein as microhydrogels. Hydrogel particle diameter may be controlled by a number of factors, including the choice of hydrogel material and components of the W/O emulsion, as well as the process used to prepare the vaccine composition. Hydrogel particle diameter may be ascertained using a range of optical techniques, such as dynamic light scattering, light microscopy and confocal laser scanning microscopy.

The hydrogel particles are dispersed in the aqueous phase of the water-in-oil emulsion. A skilled person would appreciate that the aqueous phase of the emulsion would contain an aqueous liquid. Generally, the aqueous liquid comprises water.

The hydrogel particles according to the present invention are biocompatible and are formed from biocompatible materials. Biocompatibility is a concept known to those in the art. Biocompatible substances are those that elicit acceptable immune responses. Accordingly, as used herein the term "biocompatible" refers to a substance or component that is biologically compatible such that it substantially does not elicit an adverse immune, toxic or injurious response in vivo, or adversely integrates with a particular cell type or tissue.

In addition to being biocompatible, the hydrogel particles are hydrophilic and amenable to aqueous solvation.

The hydrogel particles may comprise a suitable hydrophilic and biocompatible polymers. The polymers may be selected to be compatible with a desired immunogen that is to be delivered by the vaccine composition. By being compatible with the immunogen, the hydrogel particles do not adversely affect immunogen structure or function, and provide for the controlled or persistent release of the immunogen, and accordingly can provide a secondary longer term release stage. Polyanionic biopolymers such as alginates, hyaluronates, chondroitin sulphates, carboxymethyl cellulose can be used to construct the hydrogel particle core.

In one set of embodiments, the hydrogel particles comprise a biocompatible anionic polymer. A skilled person would appreciate that anionic polymers are polyelectrolytes that carry a net negative charge at physiological pH (approximately pH 7).

Anionic polymers may be of natural or synthetic origin and will generally contain ionisable functional groups that are capable of bearing a negative charge at physiological pH.

In some embodiments, the hydrogel particles comprise a crosslinked anionic polymer.

Crosslinked anionic polymers suitable for the hydrogel particles may be produced when an anionic polymer component reacts or interacts with a complementary crosslinking component to form a macromolecular network structure that is held together via intermolecular bonds. Suitably, the intermolecular bonds are non-covalent bonds, such as ionic bonds. The macromolecular network can thus be regarded as a crosslinked polymer matrix. The crosslinking component can be provided by a crosslinking agent, which may be a small molecule or a macromolecule, such as a further polymer.

In one embodiment, the hydrogel particles comprise a crosslinked anionic biopolymer. Biopolymers may be polymeric molecules obtained from, or derived from, natural sources.

In one embodiment, the hydrogel particles comprise a crosslinked anionic polysaccharide.

A skilled person would understand that polysaccharides are polymeric carbohydrate molecules composed of monosaccharide units linked via glycosidic linkages.

Anionic polysaccharides are a class of polysaccharide comprising ionisable functional groups (such as a hydroxyl, carboxylic acid or sulphonate group) that are capable of carrying a negative charge at physiological pH. Such polysaccharides are regarded as suitable polymer materials for the hydrogel particles described herein since they are hydrophilic, generally non-toxic and biocompatible.

Anionic polysaccharides useful for the hydrogel particles may be anionic natural polysaccharides or anionic modified polysaccharides.

Anionic polysaccharides can be combined with a suitable crosslinking agent to form a crosslinked macromolecule. It would be appreciated that the anionic polysaccharide and the crosslinking agent must be capable of interacting with one another in order to form the crosslinked polymer.

Suitable crosslinking agents may be capable of interacting with the polysaccharide via non-covalent bonding mechanisms. In such embodiments, the crosslinking agent may be capable of interacting with one or more anionic functional groups present on the anionic polysaccharide via non-covalent bonding mechanisms, such as electrostatic or ionic bonds.

The hydrogel particles of the vaccine composition may comprise a suitable anionic polysaccharide. Exemplary anionic polysaccharides can include alginate, xanthan gum, hyaluronic acid, heparin, carboxymethylated polysaccharides and sulfonated polysaccharides.

In one embodiment, the hydrogel particles comprise crosslinked alginate.

Alginate is naturally occurring polysaccharide that is isolated from seaweed and is composed of a block copolymer comprising covalently linked blocks of (1-4)-linked β-D-mannuronate (M) and α-L-guluronate (G) residues. The proportion and distribution of M and G may determine the physical and chemical properties of the alginate. In some embodiments, alginate described herein may typically have an M/G ratio of 1.56.

Alginate has biocompatibility and low toxicity and can undergo crosslinking and gelation under mild conditions. At neutral pH (approximately pH 7), alginate is anionic and carries a net negative charge.

Commercially available alginate may be provided as the salt form of alginic acid. An example is sodium alginate, which is the sodium salt form of alginic acid.

Alginate suitable for use in the hydrogel particles may be of a range of molecular weights. In some embodiments, alginate may have a molecular weight in the range of from about 40 to 270 kDa, for instance about 50 kDa, or about 60 kDa, or about 70 kDa, or about 80 kDa, or about 90 kDa, or about 100 kDa, or about 110 kDa, or about 120 kDa, or about 130 kDa, or about 140 kDa, or about 150 kDa, or about 160 kDa, or about 170 kDa, or about 180 kDa, or about 190 kDa, or about 200 kDa, or about 210 kDa, or about 220 kDa, or about 230 kDa, or about 240 kDa, or about 250 kDa or about 260 kDa. In an embodiment, the alginate may have medium viscosity of >2000 cP at a concentration of 2% in water at 25° C., with molecular weight of 80-120 kDa.

In one set of embodiments, the hydrogel particles of the vaccine composition may comprise alginate in an amount of from about 1 to 6% (w/v), for instance about 2% (w/v), or about 3% (w/v), or about 4% (w/v), or about 5% (w/v), or any range in between, depending on the molecular weight of the alginate. In some embodiments, the hydrogel particles may comprise alginate in an amount of about 2% (w/v).

Crosslinking of alginate can be induced by combining the alginate with a positively charged molecule or compound, such as a cation. Alkaline earth metal compounds provide a source of divalent cations and thus such compounds can be used as crosslinking agents to crosslink the alginate. Alkaline earth metal compounds useful as crosslinking agents may be calcium or magnesium compounds. In one embodiment the alginate may be crosslinked electrostatically with cations such as calcium ($Ca^{2+}$) or magnesium ($Mg^{2+}$).

In one preference, the hydrogel particles comprise alginate crosslinked with calcium cations. Calcium cations may participate in selective ionic bonding with guluronate residues in alginate chains to induce gel formation and crosslinking via non-covalent bonding interactions.

Calcium cations may be provided by a range of calcium compounds as crosslinking agents. Suitable calcium compounds may be selected from calcium chloride ($CaCl_2$), calcium sulphate ($CaSO_4$) and calcium carbonate ($CaCO_3$). In one preference, the calcium compound is calcium chloride.

Crosslinked alginate useful for the hydrogel particles may comprise alginate and a cation (such as a calcium cation) in a suitable molar ratio. In some embodiments, it may be desirable to vary the level of crosslinking by adjusting the ratio of alginate to cation. The control of the crosslinking degree determines the mechanical properties and the degradation rate of the microhydrogel to give a greater control over the sustained or persistent release of the particulate immunogen (e.g., antigen).

In some embodiments, the molar ratio of alginate to cation may be from about 1:0.5 to about 1:2, for instance about 1:1, or about 1:1.5. In other embodiments, the % wt/wt ratio of anionic polymer (alginate) to cation (for example $Ca^{2+}$) is from about 1:3 to about 1:7. In other embodiments, the ratio is about 1:3.5, about 1:4, about 1:4.5, about 1:5, about 1:5.2, about 1:5.4, about 1:5.6, about 1:5.8, about 1:6, or about 1:6.5. In an embodiment, the preferred ratio of alginate to cation used is 1:5.6 or 1:2.8.

The crosslinking of alginate with a cation also neutralises the negative charge carried by alginate at neutral pH. This neutralisation of negative charge allows hydrogel particles comprising alginate to efficiently contain negatively charged immunogens, which might otherwise be difficult to achieve due to the potential for unfavourable electrostatic interactions with the anionic alginate polymer.

The hydrogel particles of the vaccine composition may be of a suitable size. The size may be selected to enable the hydrogel particles to be administered with the remaining components of the vaccine composition by injection to a subject. For instance, the hydrogel particles, including a continuous shell, may have an average particle diameter in the range of from about 3 μm to 20 μm, for instance about 4 μm, or about 5 μm, or about 6 μm, or about 7 μm, or about 8 μm, or about 9 μm, or about 10 μm, or about 11 μm and so on (or any ranges formed from these figures).

The vaccine composition of the invention also comprises a biocompatible cationic polymer, which is attached to the hydrogel particles. In general, the cationic polymer will be attached to the surface of the hydrogel particles. Attachment of the cationic polymer to the hydrogel particles results in formation of a coating comprising the cationic polymer on the hydrogel.

The coated hydrogel particles therefore have an inner hydrogel component forming a core and an outer component comprising a complex of the, for instance, anionic alginate and the cationic polymer forming a coating that surrounds the hydrogel-based core. In one set of embodiments, the hydrogel-based core is a crosslinked alginate hydrogel core.

In one form of the vaccine composition, the complexed cationic polymer forms a shell that surrounds the hydrogel particle core. The shell can provide an interfacial layer that separates the particles from the water-in-oil emulsion. The shell is generally hydrophilic in nature to be compatible with the hydrogel particles and the aqueous phase of the water-in-oil emulsion in which the particles are dispersed. The presence of a shell surrounding the hydrogel particles may be discerned using various optical, imaging or spectroscopic techniques.

The cationic polymer may form a continuous shell or a non-continuous shell that surrounds the hydrogel particles. Both the continuous shell and non-continuous shell can contribute to the antigen of the primary dose, as the shell is in physical contact with alginate inner core hydrogel.

A "continuous shell" may be regarded as an unbroken layer of material.

In comparison, a "non-continuous shell" may be regarded as a discontinuous layer of material. In some embodiments, a non-continuous shell may be layer of material having one or more breaks or interruptions in the layer. In other embodiments, a non-continuous shell may be composed of multiple individual and discrete portions of material that are arranged in a layer structure.

For instance, a non-continuous shell may be composed of multiple droplets containing polymer material arranged in a single layer around a hydrogel particle. In such embodiments, the biocompatible cationic polymer may be contained in the droplets. The droplets will generally be of smaller size than the hydrogel particle in which they surround. For instance, the droplets (which ultimately form the shell) may have a diameter in the nanometre range and up to no more than about 2 μm. In some instances, the droplets may have an average diameter of approximately 1 μm. It will be appreciated that the biocompatible cationic polymer shell thickness is primarily responsible for controlling the primary release characteristics of the vaccine compositions disclosed herein.

Alternatively, a continuous shell may also result from multiple droplets containing polymer material arranged in a single layer around a hydrogel particle. The resultant continuous shell may have a diameter in the range of for instance, about 1 μm to about 3 μm. Again, it will be appreciated that the biocompatible cationic polymer shell thickness is primarily responsible for controlling the primary release characteristics of the vaccine compositions disclosed herein and can be varied to suit the primary dosing requirement.

Figure 5:
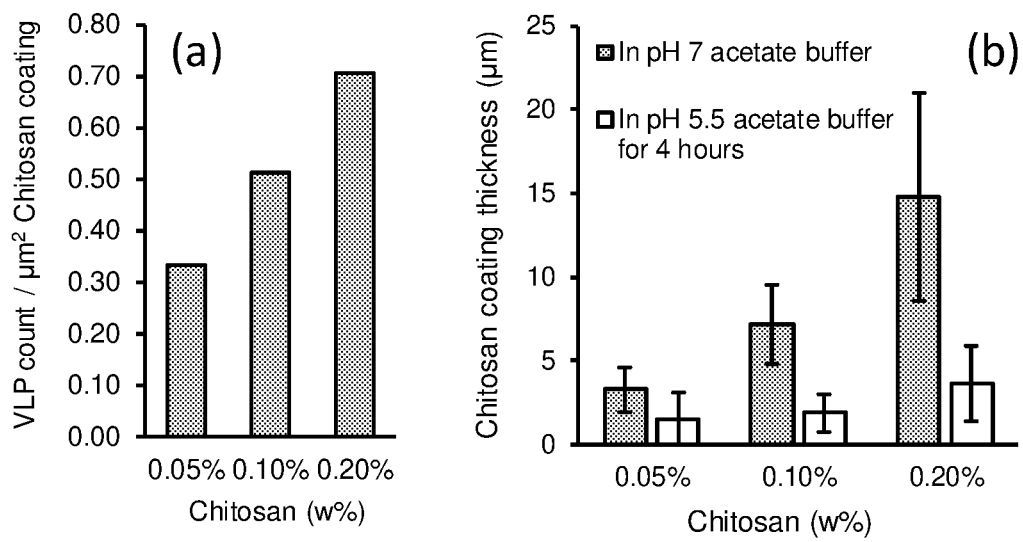
FIG. 5 shows that the profile of the chitosan and VLP populations across the encapsulation membrane as the chitosan thickness is changed to yield control of the primary dose. As the membrane thickness is increased, the quantity of VLPs encapsulated progressively increases as seen in FIG. 5 (a) which directly controls the primary immunological response upon injection. Control of VLP release within dendritic cells and macrophages during the primary phase on injection results from the effective dissolution of the chitosan membrane at the lower pH of these cellular lysosomes (FIG. 5(b)).
Figure 6:
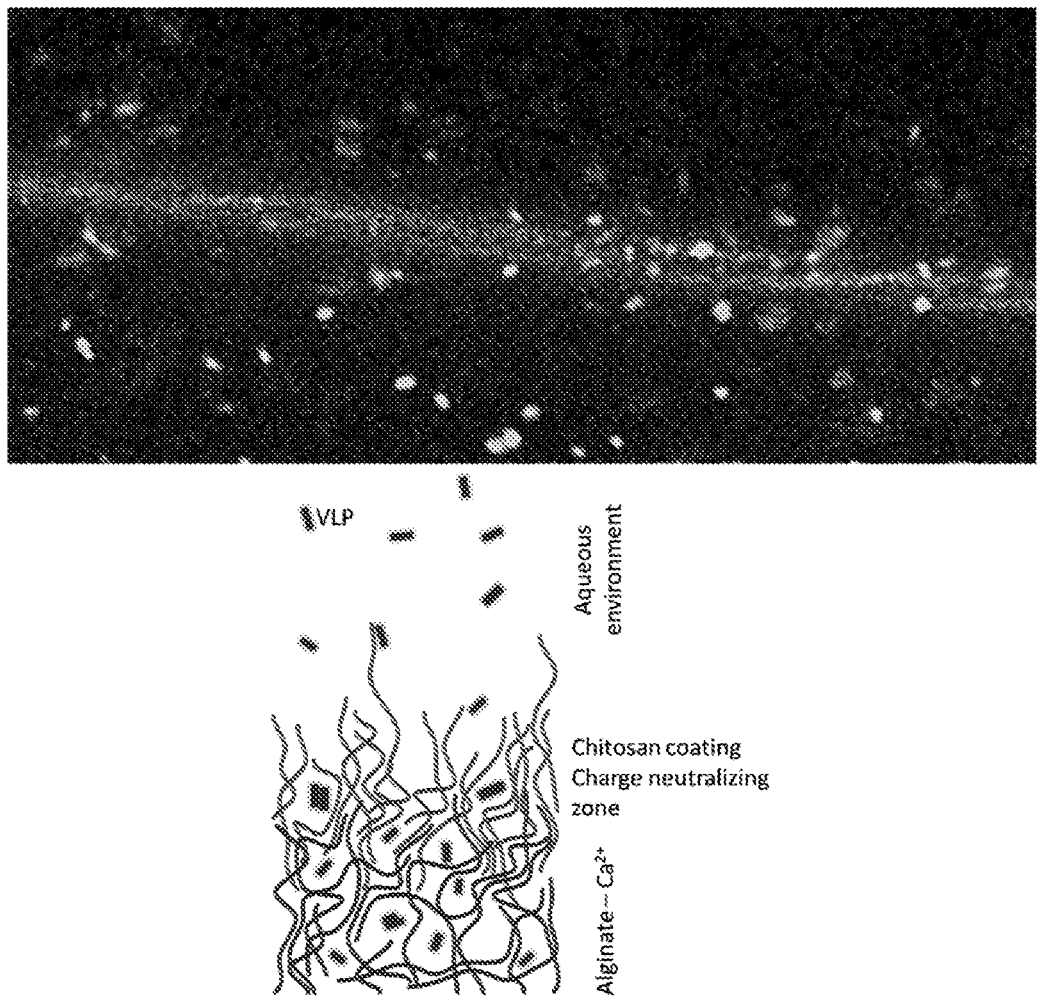
FIG. 6 shows release of the VLPs during the dissolution and thinning of the chitosan membrane of FIG. 5. The lower section of micrograph of FIG. 6 shows VLPs within the alginate depot core together with the thinning chitosan membrane and released VLPs (upper section of micrograph). This is also diagrammatically illustrated as free VLPs enter the aqueous lysozyme of these cells providing the initial primary dose. Subsequent slower enzymatic dissolution of the alginate core depot provides longer term antigen delivery and sustained immunological response.

Control of the ratio of immunogen release between the primary dose and the following sustained release is shown by quantifying the immunogen population for shell thickness (see, for instance, FIG. 5).

Accordingly, in another embodiment the invention provides a vaccine composition comprising:

a water-in-oil emulsion;

a plurality of hydrogel particles loaded with an immunogen dispersed in the aqueous phase of the water-in-oil emulsion, and a biocompatible cationic polymer attached to the hydrogel particles, wherein a portion of the immunogen is partitioned within the hydrogel particles to provide for a persistent dose and a portion of the immunogen is partitioned within the biocompatible cationic polymer attached to the hydrogel particles to provide for an initial priming dose, wherein the biocompatible cationic polymer is attached to the hydrogel particles as a continuous shell and non-continuous shell surrounding said hydrogel particles.

The cationic polymer may be attached to the hydrogel particles via covalent or non-covalent bonding interactions. The type of bonding interaction utilised for attachment of the cationic polymer to the hydrogel particles may be dictated by the composition of the hydrogel particles and the type of polymer used to form the particles.

In one form, when the hydrogel particles of the vaccine composition comprise a biocompatible anionic polymer (such as alginate), the cationic polymer can be electrostatically complexed with the anionic polymer. Thus the cationic polymer can interact with the oppositely charged anionic polymer in the hydrogel particles via ionic (i.e. non-covalent) bonding interactions to result in attachment of the cationic polymer to the particles. In such embodiments, the region where the cationic polymer electrostatically complexes with the oppositely charged anionic polymer may resemble an interpenetrating polymer network (IPN) due to entanglement of the oppositely charged polymers.

Figure 4:
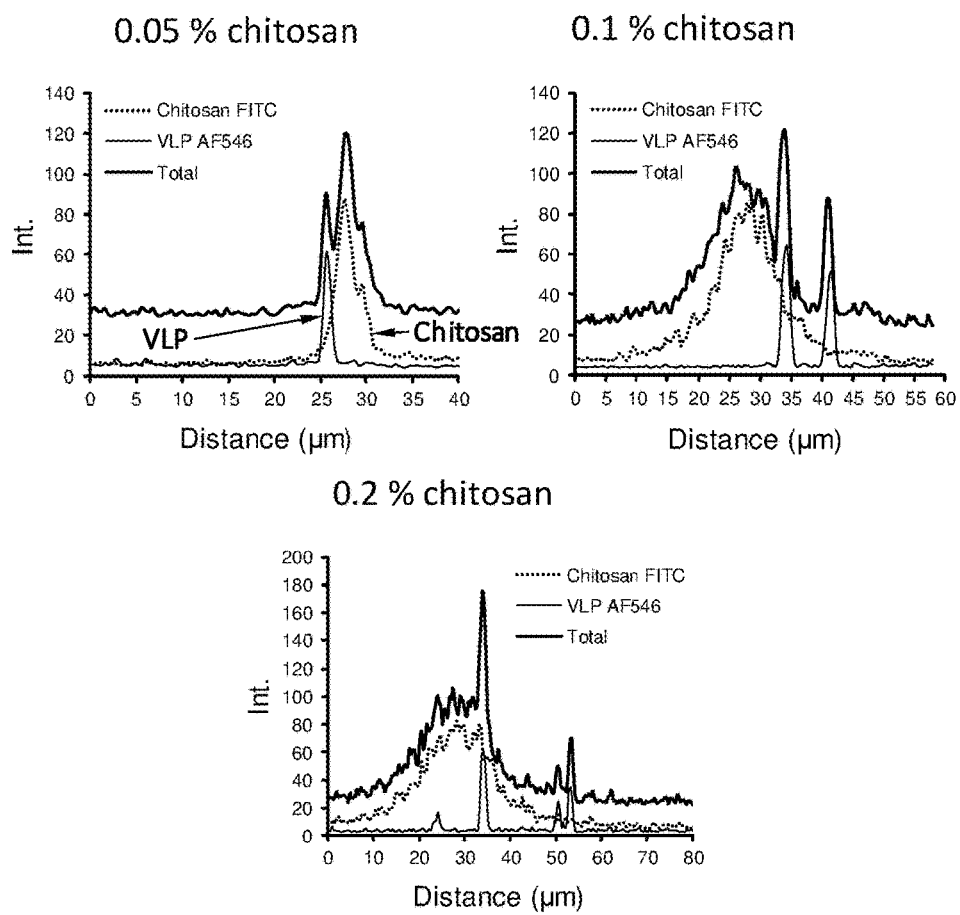
FIG. 4 shows that the thickness of the chitosan membrane on microhydrogel particles can be systematically varied via the chitosan concentration and volume present during formation. Here it can be seen that the thickness of the membrane varies between about 3 µm and 16 µm.

As shown in the examples and FIGS. 4 and 5, in some embodiments, the % wt/wt ratio of the anionic polymer to the cationic polymer is about 1:10 to about 10:1, preferably 1:4 to 4:1. The % wt/wt ratio influences the partition of the immunogen in the core as compared to the shell. Advantageously, this allows for control over the primary dose and the secondary longer term sustained or persistent release of immunogen.

A proportion of the immunogen is partitioned within the biocompatible cationic polymer. This allows the vaccine composition to perform its primary dose function. As shown in FIG. 5, for example, in some embodiments, the surface area distribution of immunogen to cationic polymer is about 0.2 particle/$\mu m^2$ to about 1 particle/$\mu m^2$. In other embodiments, the surface area distribution is about 0.3 particle/$\mu m^2$, about 0.4 particle/$\mu m^2$, about 0.5 particle/$\mu m^2$, about 0.6 particle/$\mu m^2$, about 0.7 particle/$\mu m^2$, about 0.8 particle/$\mu m^2$, about 0.9 particle/$\mu m^2$ or about 1 particle/$\mu m^2$.

The biocompatible cationic polymer may be selected from a number of suitable polymers. In one embodiment, the biocompatible cationic polymer is a cationic polysaccharide. Preferably, the cationic polysaccharide is derived from natural sources.

In one set of embodiments, the cationic polysaccharide is chitosan. This polysaccharide that is positively charged at physiological pH. A coating comprising chitosan may thus also be positively charged at physiological pH.

Chitosan is a linear polyaminosaccharide composed of randomly distributed β-(1-4)-linked D-glucosamine (a deacetylated unit) and N-acetyl-D-glucosamine (an acetylated unit). The degree of deacetylation (% DA) can be determined by NMR spectroscopy, and the % DA in commercial chitosan is in the range 60-100%, for instance 65%, or 70%, or 75%, or 80% or 85% or 90%, or 95%.

Chitosan is biocompatible, enzymatically biodegradable (for example by lysozyme hydrolysis), and non-toxic (its degradation products are relatively non-immunogenic and non-carcinogenic).

The amino group in chitosan has a pKa value of approximately 6.5. Thus, chitosan is positively charged (i.e. the amino groups are protonated) and soluble in acidic to neutral solution with a charge density dependent on pH and the % DA-value. In other words, chitosan can act as a positively charged polyelectrolyte under physiological conditions and thus has appropriate functionality to be crosslinked with a crosslinking agent.

Accordingly, in another embodiment the invention provides a vaccine composition comprising:
a water-in-oil emulsion;
a plurality of hydrogel particles loaded with an immunogen dispersed in the aqueous phase of the water-in-oil emulsion, and a biocompatible cationic polymer attached to the hydrogel particles,
wherein a portion of the immunogen is partitioned within the hydrogel particles to provide for a persistent dose and a portion of the immunogen is partitioned within the biocompatible cationic polymer attached to the hydrogel particles to provide for an initial priming dose, wherein the biocompatible cationic polymer is attached to the hydrogel particles as a continuous shell and non-continuous shell surrounding said hydrogel particles,
wherein the biocompatible cationic polymer is chitosan and the hydrogel particles comprise alignate.

The crosslinking of chitosan can be controlled. For example, tripolyphosphate (TPP) can be added to control the crosslinking of chitosan. This influences the porosity of the resultant shell and thus can be effective in controlling the release in the primary dose. The inventors have found that a specific range of crosslinking is beneficial in that the primary release can occur at its targeted release site; i.e. the immunogen is not held on too tightly or loosely in the shell.

In some embodiments, the % wt/wt ratio of cationic polymer (chitosan) to crosslinking agent (for example TPP) is from about 1:3 to about 1:7. In other embodiments, the ratio is about 1:3.5, about 1:4, about 1:4.5, about 1:5, about 1:5.2, about 1:5.4, about 1:5.6, about 1:5.8, about 1:6, or about 1:6.5.

Chitosan suitable for use in the vaccine composition of the invention may be of a range of molecular weights. In an embodiment, the chitosan is a low molecular weight chitosan having a molecular weight (Mw) of between 10-250 kDa, for instance 10 kDa, or 20 kDa, or 30 kDa, or 40 kDa, or 50 kDa, or 60 kDa, or 70 kDa, or 80 kDa, or 90 kDa, or 100 kDa, or 110 kDa, or 120 kDa, or 130 kDa, or 140 kDa, or 150 kDa, or 160 kDa, or 170 kDa, or 180 kDa, or 190 kDa, or 200 kDa, or 210 kDa, or 220 kDa, or 230 kDa, or 240 kDa. In some embodiments, the Mw is preferably in the range of 40-100 kDa, for instance 45 kDa, or 50 kDa, or 55 kDa, or 60 kDa, or 65 kDa, or 70 kDa, or 75 kDa, or 80 kDa, or 85 kDa, or 90 kDa.

In one set of embodiments, the chitosan may be present in the vaccine composition in an amount of from about 0.05 to 1% (w/v), or about 0.1 to 1% (w/v), for instance about 0.2% (w/v), or 0.3% (w/v), or 0.4% (w/v), or 0.5% (w/v) or 0.6% (w/v), or 0.7% (w/v), or 0.8% (w/v), or 0.9% (w/v), depending on the molecular weight of the chitosan. In some embodiments, the vaccine composition may comprise chitosan in an amount of about 0.5% (w/v).

In one preference, chitosan in the vaccine composition of the invention is not crosslinked and thus carries a net positive charge at physiological pH.

Chitosan has recently been shown to promote dendritic cell maturation and trigger innate and adaptive immune responses. This suggests that chitosan could be an attractive candidate adjuvant for vaccine compositions and assist in increasing the time duration in the bioavailability of the immunogen to the immune system. It is therefore believed that chitosan that is attached to and surrounding the hydrogel particles is externally confined to the particles may thus advantageously assist in providing enhanced immunogen-specific responses toward innate and adaptive immunity.

The present inventors have also found that a portion of the immunogen may be advantageously partitioned in the chitosan to provide a controlled initial priming dose (immediate release). In this embodiment, at least 20% of the immunogen is in the chitosan layer, such as at least 30, or at least 40%, or at least 50%, or at least 60%, to provide an initial priming dose.

The core of the hydrogel particles of the vaccine composition of the invention may contain the remainder of the immunogen, which is desired to be administered to a subject over an extended or delayed period. In this regard, the immunogen is partition between the shell and the core of the particle.

As used herein, the term "immunogen" describes a molecule of synthetic or natural origin, which is capable of raising an immune response in vivo. The immune response may be humoral or cell-mediated.

By hydrogel particles being "loaded" with an immunogen is meant that the particles contain the immunogen and act as a carrier for the immunogen. In one form, each hydrogel particle encapsulates an immunogen within its internal structure.

One or more immunogen VLPs may be loaded in a single hydrogel particle. In some embodiments, a hydrogel particle may contain a plurality of particulate immunogens such as virus-like particles (VLPs). Particulate immunogens in a hydrogel particle may be situated in the core of the particle and/or near the surface of the particle. In embodiments where an immunogen is situated near the surface of a hydrogel particle, it remains that the immunogen is still within the structure of the hydrogel particle.

With the loading of immunogen in the hydrogel core and the chitosan layer, one is able to realise an effective "priming" dose as the immunogen is rapidly (immediately) released from the chitosan coating layer and then a subsequent delayed and sustained dose release as the hydrogel particle is gradually degraded in vivo over time. This delayed release could be as much as 6 months to 1 year.

Representative immunogens may include, but are not limited to, natural, recombinant or synthetic products derived from viruses, bacteria, fungi and parasites, and fragments or portions thereof. The hydrogel particles may be loaded with one or more of these immunogens.

In one set of embodiments, the immunogen may be a particulate immunogen. Examples of particulate immunogens include virus-like particles (VLP), pathogen mimicking particles and bacterial vaccines (either killed or attenuated).

Immunogens in the vaccine composition of the invention may carry a net charge at physiological pH. In one embodiment, the immunogen carries a net negative charge at physiological pH.

In one embodiment of the vaccine composition, the immunogen is a virus-like particle. In one preference, the immunogen is a virus-like particle (VLP) containing a suitable antigen.

In one set of embodiments, the immunogen is a virus-like particle selected from the group consisting of Hepatitis B, Hepatitis E, human papilloma virus, chikungunya virus, influenza, foot and mouth disease (FMD), human immunodeficiency virus (HIV), Zika virus, *Actinobacillus pleuropneumoniae* (previously *Haemophilus pleuropneumoniae*), *Haemophilus parasuis* (*H. parasuis*), *Streptococcus suis*, Foot and Mouth Disease (FMD), Cattle Viral Diarrhea (Pestivirus) (BVDV), Bovine herpesvirus (BHV-1) causing Infectious bovine rhinotracheitis (IPV) and/or Infectious pustular vulvovaginitis (IPV), and Rabies.

In certain embodiments of the vaccine composition described herein, chitosan is attached to the hydrogel particles and can advantageously act as an adjuvant to promote a desired immune response. However, where the immunogen is negatively charged, the chitosan may adversely affect the immunogen, as the structure of the immunogen may be disrupted or destroyed due to interactions with the positively charged chitosan at physiological pH. For this reason, the loading of the immunogen in hydrogel particles that are inert or similar in charge to the immunogen can help to mitigate any adverse impact the chitosan may have on the potency or activity of the immunogen.

As indicated above, the vaccine composition of the invention comprises a water-in-oil (W/O) emulsion comprising an aqueous phase dispersed in an oil phase.

In one set of embodiments, the water-in-oil emulsion may be part of a multiple emulsion, such as a double emulsion where the oil (O) phase enclosing water (W) droplets is further dispersed in a secondary water (W) phase. Such an emulsion is known as a water-in-oil-in-water (W/O/W) emulsion.

The oil phase of the emulsion comprises at least one metabolisable oil and may comprise a mixture of such oils. A metabolisable oil may be a physiologically acceptable oil. Physiologically acceptable oils are generally hydrophobic and liquid at a temperature between 20° C. and 40° C.

In some embodiments, the oil phase may comprise one or more oils selected from the group consisting of fatty acids; fatty acid esters; esters of polyethylene glycols, for example mono- and di-esters; hydrocarbon oils, for example natural hydrocarbon oils; and steroids, for example cholesterol.

Suitable fatty acids and fatty acid esters may be those having an aliphatic saturated or unsaturated chain comprising from 6 to 24 carbon atoms. Unsaturated aliphatic chains may be mono- or poly-unsaturated. Some particular fatty acids may be long chain $C_{12}$-$C_{24}$ fatty acids e.g. $C_{15}$-$C_{22}$ fatty acids, and medium chain $C_6$-$C_{12}$ fatty acids. Among these, include poly-unsaturated fatty acids such as omega-3 oils, for example, eicosapentanoic acid (EPA), docosohexaenoic acid (DHA), alpha-linoleic acid (ALA). Combinations of such compounds are also contemplated. Fatty acid esters may be triglycerides, as well as esters of glycerol (particularly tri-esters) with a combination of fatty acids and lower molecular weight acids e.g. succinic acid (fatty acid triglycerides are a particular example of glycerides). Oils containing triglycerides may also contain mono- and/or di-glycerides, e.g. as a minor part of the glyceride content (less than 50 mol %).

In some embodiments, the oil phase may comprise a mixture of oils, for example fatty acid macrogolglycerides, also known as polyoxylglycerides, which are mixtures of fatty acid monoesters, diesters and triesters of glycerol and fatty acid monoesters and diesters of polyethylene glycol; examples are oleoyl macrogolglycerides and linoeoyl macrogolglycerides.

Suitable hydrocarbon oils may be mineral oils or terpenes.

Particular terpenes may be triterpenes such as, for example, squalene.

Particular mineral oils may comprise a mixture of several hydrocarbon chains of different lengths, including small chains (≤C14) and longer chain (>C14) hydrocarbon lengths. Examples of mineral oils of a pharmaceutical grade include light liquid paraffin and light mineral oil.

Alternative or additional oils, which may be included in the oil phase in combination with or in place of the above oils include plant or vegetable oils, such as peanut oil, safflower oil, sunflower oil, soya bean oil, cottonseed oil, chaulmoogra oil, corn oil, jojoba oil, pesic oil, olive oil, sesame oil, almond oil, castor oil, canola oil, linseed oil, squalene and coconut oil; fish oils such as shark oil, orange roughy oil, Menhaden oil and cod liver oil; animal oils such as mink oil, lard oil and chicken fat oil; and synthetic oils such as ethyl oleate.

Adjuvants are used in vaccine compositions to enhance a subject's physiological response to an immunogen. For example, an adjuvant may act to enhance a subject's immune response to the immunogen by increasing antibodies and thus the longevity of the immune response.

In some embodiments, the oil per se can be an adjuvant and thus the oil phase of the emulsion comprises an adjuvanting oil. The use of an adjuvanting oil may be desirable to augment the adjuvanting properties of the chitosan which surrounds the immunogen loaded hydrogel particles in the vaccine composition of the invention. Examples of adjuvanting oils include mineral and non-mineral oils.

In alternative embodiments, the oil phase may comprise a lipophilic adjuvant dissolved or suspended in a non-adjuvanting (passive) oil.

Various adjuvants are known to those skilled in the art and a skilled person would appreciate that the selection of a particular adjuvant might depend on the immunogen to be delivered to a subject, the disease or disorder targeted by the vaccine composition.

In one embodiment, the emulsion of the vaccine composition has adjuvanting properties. In some embodiments, the emulsion may comprise or be composed of one or more commercially available adjuvant oils to produce a W/O or W/O/W emulsion preparation. Commercially available adjuvant preparations generally contain a mineral oil or a combination of oils, optionally together with other components. Such commercial preparations may also desirably contain one or more surfactants or emulsifiers to stabilise the emulsion. In such circumstances, the vaccine composition of the invention will also contain the surfactant or emulsifier as part of the composition. Examples of commercial adjuvant preparations include the Montanide™ series of adjuvants from Seppic. Particular examples of Montanide™ adjuvants include Montanide™ ISA 61 VG, which can produce a W/O emulsion comprising a light mineral oil and an emulsifier comprising mannitol and oleic acid, and Montanide™ ISA 201 VG, which can produce a W/O/W emulsion preparation. Other commercial adjuvant formulations suitable for producing W/O or W/O/W emulsions may also be used. Commercially available adjuvant preparations may be selected to suit a particular immunogen.

In another aspect of the invention there is provided a vaccine composition comprising:
  a water-in-oil emulsion;
  a plurality of alginate particles loaded with virus-like particles (VLP) dispersed in the aqueous phase of the water-in-oil emulsion, and
  chitosan surrounding and complexed with the alginate particles.

In another embodiment of the invention there is provided a vaccine composition comprising:
  a water-in-oil emulsion;
  a plurality of alginate particles loaded with a particulate immunogen (e.g., virus-like particles (VLPs)) dispersed in the aqueous phase of the water-in-oil emulsion, and
  chitosan surrounding and complexed with the alginate particles, wherein a portion of the immunogen is partitioned within the alginate particles to provide for a persistent dose and a portion of the immunogen is partitioned within the chitosan surrounding and complexed with said alginate particles to provide for an initial priming dose.

In one preference of the above aspect, the water-in-oil emulsion comprises a Montanide™, such as Montanide™ ISA 61 VG or Montanide™ ISA 201 VG.

If desired, the vaccine composition of the invention may optionally comprise one or more additional components. The additional components may be employed to modify the properties of the vaccine composition of the invention, and may be, for example, salts or ions to adjust the pH or ionic strength of the aqueous phase, surfactants, emulsifiers, further adjuvants, and the like. When present, the additional components may be contained in the oil phase and/or the aqueous phase of the water-in-oil emulsion described herein, including in the hydrogel particles and/or in a shell surrounding the hydrogel particles.

As discussed above, when the water-in-oil emulsion of the vaccine composition may comprise a surfactant. The surfactant may be present in commercial adjuvant preparations that are used to provide the W/O emulsion of the vaccine composition. The presence of surfactants in the vaccine composition may help to reduce or prevent complete phase separation of the aqueous and oil phases of the emulsion and thus aid in the production of a more stable vaccine composition.

Surfactants may be present in an amount of up to 5% by weight of the vaccine composition. In some embodiments, the surfactant may be present in an amount of up to 1% by weight of the vaccine composition.

Various pharmaceutically acceptable surfactants are known to one skilled in the art.

The advantages of the system described herein are: (1) protection of the immunogen, e.g., VLP, in the period of vaccine storage and after administration until they reach their intended target cells, (2) providing of an initial "priming" dose (immediate release), (3) increase in circulation time after administration to a subject to provide prolonged immune response, and (4) enhanced immune response and induction of both humoral and adaptive immunity.

The vaccine composition of the invention can be prepared using equipment and techniques suitable for forming emulsion compositions, in particular, water-in-oil emulsions.

In one aspect, the present invention provides a process for preparing a vaccine composition of any one of the embodiments described herein, the process comprising the steps of:
  emulsifying an aqueous composition comprising a first hydrogel forming component and an immunogen with a first portion of oil to give a water-in-oil emulsion composition under a first condition and form a first emulsified composition;
  emulsifying an aqueous composition comprising a second hydrogel forming component and a biocompatible cationic polymer with a second portion of oil to give a water-in-oil emulsion composition under a second condition and form a second emulsified composition;
  combining the first emulsified composition and the second emulsified composition under conditions allowing the first hydrogel forming component to react with the second hydrogel forming component and the cationic polymer to form the hydrogel coating layer and produce a plurality of immunogen loaded hydrogel particles having the cationic polymer attached thereto in situ and thereby provide a vaccine composition comprising a water-in-oil emulsion and immunogen loaded hydrogel particles comprising a cationic polymer attached to the hydrogel particles dispersed in the aqueous phase of the emulsion.

One form of the process described herein comprises a step of providing a water-in-oil emulsion to form the vaccine composition. The provided water-in-oil emulsion composition may be a commercially available adjuvant preparation suitable for a particular immunogen. An example is a Montanide™ preparation, as described herein. In one set of the embodiments, the water-in-oil emulsion composition may be Montanide™ ISA 61 VG or Montanide™ ISA 201 VG.

In preparing the vaccine composition, portions of the water-in-oil emulsion composition are initially separately emulsified with different aqueous compositions to form separate emulsified compositions. The emulsified compositions are subsequently combined to form the vaccine composition of the invention.

To form a first emulsified composition, a first portion of the water-in-oil emulsion can be combined with a first aqueous composition. In such embodiments, the aqueous composition may comprise a first hydrogel forming component and an immunogen. The first hydrogel forming component may be a biocompatible anionic polymer as described herein. The anionic polymer may be present in the composition in an amount in a range of from about 1 to 6 wt %, depending on the molecular weight of the polymer. In one embodiment, the anionic polymer is present in the aqueous composition in an amount of about 2 wt %.

In one exemplary embodiment, the first aqueous composition comprises alginate and an immunogen. The immunogen may be a particulate immunogen, such as an antigen within a VLP.

The first aqueous composition is emulsified in oil to give a water-in-oil emulsion composition under a first condition to form a first emulsified composition.

In one set of embodiments, the first aqueous composition may be emulsified in oil to give the water-in-oil emulsion composition under conditions of high shear. High shear conditions can advantageously be employed to form aqueous droplets of desired particle size in the first emulsified composition.

In one set of embodiments, a first aqueous composition containing a desired quantity of first hydrogel forming component and in immunogen is combined with the oil phase in a volumetric ratio of about 1:1 under a high shear condition for a desired period of time to form a first emulsified composition containing droplets of the aqueous composition of a desired size. In one form, high shear mixing of the first aqueous composition and the oil may be conducted at 11,000 rpm to provide the emulsion. Mixing of the first aqueous composition and the water-in-oil emulsion at high shear rates may produce aqueous droplets having an average particle size in the range of from about 2 to 10 µm dispersed in the first emulsified composition. In some embodiments, droplet particle size may vary depending on polymer concentration and molecular weight.

In another set of embodiments, the first aqueous composition and oil may be combined by passing them through a porous membrane to form the first emulsified composition. In such embodiments, the pore size of the porous membrane determines the size of the aqueous droplets dispersed in the first emulsified composition. Such aqueous droplets may be of a larger size than those produced under the high shear mixing conditions described above. For example, aqueous droplets produced under these conditions may have a particle size in the range of from about 3 to 15 µm.

To form the second emulsified composition, a second aqueous composition is emulsified in a second portion of the oil to give a water-in-oil emulsion and form a second emulsified composition. In such embodiments, the second aqueous composition may comprise a second hydrogel forming component and a biocompatible cationic polymer.

The second hydrogel forming component may be a crosslinking agent that is capable of reacting with the first hydrogel forming component to form a crosslinked polymer. In one exemplary embodiment, the second aqueous composition comprises a calcium compound as a crosslinking agent. The calcium compound in the may be calcium chloride ($CaCl_2$). Calcium chloride may be present in the second aqueous composition in an amount in a range of from about 2 to 3 wt %.

The second aqueous composition also comprises a biocompatible cationic polymer. As discussed herein, chitosan is an exemplary cationic polymer. In such embodiments, the chitosan may be present in the second aqueous composition in an amount in a range of from about 0.1 to 1 wt %, depending on the molecular weight of the polymer. In one embodiment, the chitosan is present in the second aqueous composition in an amount about 0.5 wt %.

In some embodiments, the first aqueous composition and the second aqueous composition may be of different viscosity. The difference in viscosity may be due to the type and quantity of polymer contained in the respective aqueous compositions, as well as polymer molecular weights. In general, solutions containing higher molecular weight polymers would have higher viscosity.

In one set of embodiments, the first aqueous composition is of higher viscosity than the second aqueous composition. The difference in viscosity may be of benefit when the components of the different aqueous compositions are eventually combined during the process described herein to form the vaccine composition.

The conditions employed for forming the second emulsified composition may be the same or different from those used to form the first emulsified composition described above. The choice of emulsification conditions may be dependent on the stability of the selected immunogen.

In one set of embodiments, higher shear conditions may produce smaller aqueous droplets in the second emulsified composition. For example, high shear conditions employed for forming the second emulsified composition may produce aqueous droplets having particle sizes in the range of from about 500 nm to 2 µm in the second emulsified composition.

The first emulsified composition and the second emulsified composition are then combined under conditions allowing the first hydrogel forming component to react with the second hydrogel forming component to form a plurality of hydrogel particles in situ. Equal volumes of the first emulsified composition and the second emulsified composition may be combined together.

Any suitable technique may be used to combine the different emulsified compositions. In some embodiments, the first emulsified composition may be added to the second emulsified composition dropwise and the combined mixture stirred together for a desired time period.

In some embodiments, the conditions under which the first emulsified composition and the second emulsified composition are may be selected to enable the anionic polysaccharide in the first emulsified composition to react with the crosslinking agent in the second emulsified composition and thereby result in colloidal portions of crosslinked hydrogel being formed in situ. The immunogen present in the first emulsified composition also becomes encapsulated in the hydrogel particles as they form. Crosslinking of the polysaccharide and the formation of hydrogel particles can occur spontaneously without the need for additional curing mechanisms or apparatus (e.g. by UV, IR, heat).

During hydrogel particle formation, the cationic polymer in the second emulsified composition spreads on the surface of the formed or forming hydrogel droplet during the combination of the first emulsified composition and the second emulsified composition. The ability of the cationic polymer to spread on the surface of the hydrogel results from the difference in viscosity of the respective composition droplets in their emulsions together with the difference in the rates of crosslinking of the components in the second emulsified composition (i.e. $Ca^{2+}$ ions versus chitosan polymer chains). For example, the rapid crosslinking of alginate by calcium ions precludes the diffusion of chitosan to the core of the alginate containing hydrogel, thus confining the cationic chitosan to an electrostatic complex with outer anionic alginate chains.

Any excess cationic polymer not attached to the hydrogel particles may be removed using conventional techniques known to a person skilled in the art prior to use of the vaccine composition.

The first emulsified composition and the second emulsified composition may be combined by mixing the different compositions under a low shear condition at a desired temperature and for a desired period of time. In one set of embodiments, the first emulsified composition and the second emulsified composition are combined by mixing the compositions at 400 rpm for a time period in the range of from 4 to 12 hours at room temperature (approximately 20° C.).

The resulting vaccine composition is therefore a water-in-oil emulsion containing a plurality of immunogen loaded and cationic polymer coated hydrogel particles, where the particles are dispersed in the aqueous phase of the emulsion.

As an illustration, a first aqueous composition comprising alginate and model VLP may be combined with Montanide™ ISA61 under shear to form a first emulsified composition. A second aqueous composition comprising chitosan and calcium chloride ($CaCl_2$) may also be combined with Montanide™ ISA61 under shear to form a second emulsified composition. The first emulsified composition is added dropwise to the second emulsified composition, then the resulting mixture is stirred for about 4 hours. Calcium cations interact with the alginate to crosslink the alginate and form colloidal portions of alginate-$Ca^{2+}$ hydrogel containing the VLP. Meanwhile, chitosan can interact with anionic alginate to become electrostatically complexed to the hydrogel particles and become attached to the surface of the colloidal hydrogel. The resulting composition is a water-in-oil emulsion vaccine formulation comprising colloidal portions of VLP loaded and chitosan coated hydrogel in the dispersed aqueous phase.

In some embodiments, formation of microhydrogels in the presence of W/O emulsion adjuvants such as the Montanide series may be dependent on the surfactant content of the respective adjuvant. The emulsification process used to prepare the vaccine composition may be tailored to enable suitable hydrogel particles to be formed.

If other components are desired to be present in the injectable composition, such components may be incorporated in one or more of the first aqueous composition, the second aqueous composition and/or in the oil used to prepare the vaccine composition.

The vaccine composition of the invention may be prepared in a one-step process, which provides a simple and effective method of production. Conventional manufacturing equipment and apparatus can be used to prepare the composition, which aids in reducing production costs.

The vaccine composition of embodiments described herein, which may be prepared in accordance with processes described herein, is capable of being administered to a subject by injection for the delivery of the immunogen to the subject. It is suitably administered in a single injection. Advantageously, the vaccine composition may be used as prepared, without the need for additional isolation, purification or formulation steps to be performed. For instance, the present invention avoids the need to isolate the hydrogel particles and to re-formulate the isolated hydrogel particles in a suitable pharmaceutically acceptable carrier or vehicle prior to their administration to a subject. However, a skilled person would appreciate that processes such as sterilisation may be carried out in relation to the vaccine composition to ensure that it complies with relevant safety or regulatory requirements.

The vaccine composition of embodiments described herein is of a viscosity that is suitable for administration by injection to a subject.

The vaccine composition can elicit a desired immune response and can promote sustained immunity against a pathogen over a period of time. The sustained immune response may be potentiated by components in the vaccine composition having adjuvanting properties. As discussed herein, the water-in-oil emulsion and the biocompatible cationic polymer present in the vaccine composition can possess adjuvanting properties.

Once the vaccine composition is administered to a subject, the immunogen loaded hydrogel particles may be internalized in macrophages and dendritic cells. The hydrogel particles may then be lysed to release the immunogen into the cytoplasm of the antigen presenting cells (APC).

In still a further aspect the invention provides a method of delivering an immunogen to a subject for the treatment or prevention of a disease or disorder in the subject, the method comprising the step of administering a vaccine composition as described herein to the subject by injection.

The injection may be subcutaneous, intramuscular or intraperitoneal. Preferably, administration is via subcutaneous injection.

The vaccine composition of the invention may be administered to a subject in order to treat or prevent a disease or condition. As used herein the terms "treating" and "preventing" mean any treatment of prevention of a disease or condition in a subject. "Treatment" and "prevention" includes: (a) controlling or inhibiting the disease or condition, i.e., arresting its development or progression; or (b) relieving or ameliorating the symptoms of the disease or condition, i.e., cause regression of the symptoms of the disease or condition. The effect may be prophylactic or therapeutic in terms of a partial or complete cure of the disease or condition.

"Disease" as used herein is a general term used to refer to any departure from health in which a subject suffers and which can be treated or prevented by the vaccine composition. A "condition" refers to an abnormal function of part of the body of a subject and which can be treated or prevented using the vaccine composition.

In another aspect the present invention provides a method of treating or preventing a disease or disorder in a subject comprising the step administering a vaccine composition of one or more embodiments as described herein to the subject by injection.

The subject in which a disease or condition is to be treated or prevented may be a human or an animal of economical importance and/or social importance to humans, for instance, carnivores other than humans (such as cats and dogs), swine (pigs, hogs, and wild boars), ruminants (such as cattle, oxen, sheep, giraffes, deer, goats, bison, and camels), horses, and birds including those kinds of birds that are endangered, kept in zoos, and fowl, and more particularly domesticated fowl, e.g., poultry, such as turkeys, chickens, ducks, geese, guinea fowl, and the like, as they are also of economical importance to humans. The term does not denote a particular age. Thus, both adult and newborn subjects are intended to be covered.

In particular embodiments, the subject is a livestock animal, such as cattle, sheep or pigs, and the disease or disorder is foot and mouth disease. In such embodiments, the vaccine composition may be considered to be a veterinary composition, and the immunogen contained in the composition is selected for the treatment or prevention of foot and mouth disease in the livestock animal.

The present invention also provides use of a vaccine composition of one or more embodiments as described herein in the manufacture of a medicament for the treatment or prevention of a disease or disorder in a subject.

In some embodiments of the method or use described herein, the immunogen is a particulate immunogen, more specifically a virus-like particle. A particular immunogen is foot and mouth disease virus-like particle.

The vaccine composition may suitably be administered to a subject such as a human or animal for delivery of a virus-like particle (VLP) to elicit an immune response.

As used in the subject specification, the singular forms "a", "an" and "the" include plural aspects unless the context clearly dictates otherwise. Reference to "the invention" includes single or multiple aspects of the invention.

Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

The invention will now be described with reference to the following examples. However, it is to be understood that the examples are provided by way of illustration of the invention and that they are in no way limiting to the scope of the invention.

EXAMPLES

Materials

The following materials were evaluated in the formulation studies: Alginate The sodium salt (low and medium and high viscosity (Sigma, Fluka and Alfa Aesar)), chitosan (low molecular weight (Sigma)), $CaCl_2$ (analytical grade, Sigma), Montanide ISA 201 VG and Montanide ISA 61 VG adjuvant oils (Seppic, France). Polycarbonate membrane with 5 µm pore diameter was from Sterlitech (US). High shear emulsification was carried out with a MICCRA (Germany) with a 8 mm stator/rotor tool. Alexa Fluor™ 546 NHS Ester was from Invitrogen, Thermo Fisher, and fluorescein isothiocyanate isomer I (FITC) was from Sigma. BacPAK™ Baculovirus was from Clonteck.

Methods

Alginate was dissolved in water to give a 4 wt % stock solution. The solution was centrifuged at 16000× g for 1 hour to remove debris and then autoclaved (temperature ramp to 121° C. in 30 min, maintaining 121° C. for 16 min followed by cooling over 30 min). If alginate solution remained turbid it was centrifuged again for 1 hour as before to give a clear solution. Chitosan stock solution was prepared at 2 wt % which was centrifuged, autoclaved and centrifuged again as above. $CaCl_2$ solution was prepared at 5.6 wt %. with solution filtered through 0.21 µm Nylon syringe filter for sterilization.

Virus-like particles (VLPs) were prepared from Baculovirus and were dispersed in a 2 wt % aqueous alginate solution with appropriate dose of VLP.

Chitosan solution and the $CaCl_2$ solution were mixed with the appropriate dilution in water to give an aqueous solution containing 0.5% chitosan and 2.6% $CaCl_2$ cross-linking solution.

To visualise the microhydrogel produced in the vaccine formulation using confocal microscopy, chitosan was labelled using FITC and VLPs were labelled using Alexa Fluor™ 546 NHS Ester. FITC-labelled chitosan was prepared according to (Qaqish and Amiji, 1999, *Carbohydrate Polymers*, 38, 99-107). Briefly, 1 g of chitosan was dissolved in 100 ml of 0.10 M acetic acid. To this solution, 100 ml of dehydrated methanol was slowly added with continuous stirring. FITC, dissolved in methanol at 1.0 mg/ml concentration, was slowly added to the chitosan solution. Reaction was continued in the dark at room temperature for 1 hour. FITC labelled chitosan was precipitated using 0.1 N NaOH and washed with deionised water extensively. The chitosan solution used to prepare microhydrogel in emulsion contained 1:10 mass ratio of labelled:unlabelled chitosans. VLPs were ladled according to manufacturer's protocol, briefly, dissolve Alexa Fluor™ 546 NHS Ester in DMF to give 10 mg/mL concentration, 50 µL of this solution was added to ~10 mg of VLP in 1 mL 0.1 M carbonate buffer at pH 8.3 and stirred in dark for 1 hour.

The control over the hydrogel microstructure design was investigated in bulk hydrogel phase by detailed study of the interfaces of alginate—chitosan and chitosan—aqueous environment. The bulk hydrogels were prepared in microscopy wells by placing 20 µL of 1% w alginate solution containing Alexa Fluor™ 546 labelled VLPs on the slide followed by the addition of 100 µL of the cross-linking solution containing $CaCl_2$ (2.8% w) and chitosan at concentrations varying between 0.05% w and 0.2% w to submerge the alginate droplet, which gelled immediately. In some examples, tripolyphosphate (TPP) was added to the alginates solution at various concentrations to increase the cross-linked chitosan fraction of the hydrogel. The excess external aqueous phase surrounding the hydrogel was replaced with 0.1 M acetate buffer solution at pH 7.0, 5.5 and 4.5 to investigate the dissolution of the chitosan encapsulating membrane and VLP release.

Example 1

Vaccine Composition with Model VLP Hydrogel Particles in Montanide ISA 201 VG W/O Emulsion Adjuvant Three different component solutions were prepared:
Part [A]: Model VLP prepared from Baculovirus was dispersed in a 2 wt % aqueous alginate solution;
Part [B]: Chitosan solution and $CaCl_2$ were mixed with the appropriate dilution in water to give an aqueous solution containing 0.5% chitosan and 2.6% $CaCl_2$;
Part [C]: Montanide ISA 201 VG To prepare the vaccine composition, a quantity of solution [A] was initially emulsified with a quantity of adjuvant oil [C] in a 1:1 volumetric ratio using MICCRA high shear emulsifier at 11,000 rpm rate for about 2 min, forming a first emulsified composition. A desired quantity of solution [B] was then separately emulsified with a quantity of adjuvant oil [C] in a 1:1 volumetric ratio at 20,000 rpm rate for about 2 min, to form a second emulsified composition. The shear rate was reduced to 11,000 rpm and the first emulsified composition was then added dropwise to the second emulsified composition under constant shearing at the same rate as before (2-3 min). To complete the cross-linking process and formation of the hydrogel particles, the final dispersion was stirred at 400 rpm using a magnetic stirrer for 4 hours, resulting in formation of the vaccine composition.

Fluorescently labelled and model VLP loaded hydrogel particles prepared in this example were assessed using confocal microscopy. The results are shown in FIG. 1.

As seen in FIG. 1, the overall size distribution of microhydrogels is given together with images and dimensions of the constructs showing a large (7 μm) model microhydrogel which provides details of its structure where fluorescently labelled chitosan (green) and VLPs (red) are clearly shown together with images of microhydrogels in the 2 to 4 micron range.

Example 2

Vaccine Composition Model VLP Hydrogel Particles in Montanide ISA 61 VG W/O Emulsion Adjuvant Three different component solutions were prepared:

Part [A]: Model VLP prepared from Baculovirus was dispersed in a 2 wt % aqueous alginate solution;

Part [B]: Chitosan solution and $CaCl_2$ were mixed with the appropriate dilution in water to give an aqueous solution containing 0.5% chitosan and 2.6% $CaCl_2$;

Part [C]: Montanide ISA 61 VG

To prepare the vaccine composition, a quantity of solution [A] was initially emulsified with a quantity of solution [C] in a 1:1 volumetric ratio using a polycarbonate membrane with 5 μm pore diameter, forming a first emulsified composition containing aqueous droplets of about 5 to 10 μm in diameter. A desired quantity of solution [B] was then separately emulsified with a quantity of adjuvant oil [C] in a 1:1 volumetric ratio at 20,000 rpm rate for about 2 min, to form a second emulsified composition containing aqueous droplets of about 1 μm in diameter. The first emulsified composition was then added dropwise to the second emulsified composition with continuous stirring at 400 rpm. To complete the cross-linking process and formation of the hydrogel particles, the final dispersion was stirred at 400 rpm using a magnetic stirrer for 12 hours. The final vaccine composition contained VLP loaded microhydrogel having an average particle size range of from about 1 to 6 μm.

Fluorescently labelled and model VLP loaded hydrogel particles prepared in this example were assessed using confocal microscopy. The results are shown in FIG. 2.

FIG. 2 shows the produced microhydrogels with the encapsulated VLPs, and chitosan-$Ca^{2+}$ droplets of about 1 μm in diameter confined electrostatically externally to the VLP loaded alginate particles. Excess (free) chitosan-$Ca^{2+}$ droplets may also be seen in the medium around the alginate hydrogel particles. On the removal of excess chitosan-$Ca^{2+}$ droplets by centrifugation and subsequent washing using the Montanide ISA61 VG, clear crosslinked alginate particles were obtained with a shell composed of chitosan on the surface as seen in FIG. 2(D).

It is to be understood that various other modifications and/or alterations may be made without departing from the spirit of the present invention as outlined herein.

The invention claimed is:
1. A vaccine composition comprising:
   a water-in-oil emulsion;
   a plurality of hydrogel particles loaded with an immunogen dispersed in the aqueous phase of the water-in-oil emulsion, and
   a biocompatible cationic polymer attached to the hydrogel particles;
   wherein a portion of the immunogen is partitioned within the hydrogel particles to provide for a persistent dose and a portion of the immunogen is partitioned within the biocompatible cationic polymer attached to the hydrogel particles to provide for an initial priming dose.

2. A vaccine composition according to claim 1, wherein that substantially all of the immunogen is sequestered in the hydrogel particles and/or in the biocompatible cationic polymer.

3. A vaccine composition according to claim 1, wherein the cationic polymer is attached as a continuous shell surrounding the hydrogel particles.

4. A vaccine composition according to claim 1, wherein the cationic polymer is attached as a non-continuous shell surrounding the hydrogel particles.

5. A vaccine composition according to claim 3, such that control is achieved over the ratio of primary dose and the sustained release dose by control of the weight ratio of the hydrogel particle core to the surrounding shell.

6. A vaccine composition according to claim 1, wherein the portion of the immunogen partitioned within the biocompatible cationic polymer is characterised to be about 5% to 70% of the total immunogen dose within the composition.

7. A vaccine composition according to claim 1, wherein the hydrogel particles comprise a biocompatible anionic polymer and the cationic polymer is electrostatically complexed with the anionic polymer.

8. A vaccine composition according to claim 7, wherein the % wt/wt ratio of the anionic polymer and cationic polymer is about 1:10 to about 10:1, preferably about 1:4 to about 4:1.

9. A vaccine composition according to claim 7, wherein the hydrogel particles comprise a crosslinked anionic polysaccharide.

10. A vaccine composition according to claim 9, wherein the hydrogel particles comprise crosslinked alginate.

11. A vaccine composition according to claim 1, wherein the cationic polymer is a cationic polysaccharide.

12. A vaccine composition according to claim 11, wherein the cationic polysaccharide is chitosan.

13. A vaccine composition according claim 1, wherein the immunogen is a particulate immunogen.

14. A vaccine composition according to claim 13, wherein the particulate immunogen is a virus-like particle, pathogen mimicking particle, or bacterial vaccine.

15. A vaccine composition according to claim 14, wherein the immunogen is a virus-like particle selected from the group consisting of Hepatitis B, Hepatitis E, human papilloma virus, chikungunya virus, influenza, foot and mouth disease (FMD), human immunodeficiency virus (HIV), Zika virus, *Actinobacillus pleuropneumoniae* (previously *Haemophilus pleuropneumoniae*), *Haemophilus parasuis* (*H. parasuis*), *Streptococcus suis*, Foot and Mouth Disease (FMD), Cattle Viral Diarrhea (Pestivirus) (BVDV), Bovine herpesvirus (BHV-1) causing Infectious bovine rhinotracheitis (IPV) and/or Infectious pustular vulvovaginitis (IPV), and Rabies.

16. A vaccine composition according to claim 1, wherein the water-in-oil emulsion comprises an adjuvanting oil.

17. A vaccine composition according to claim 16, wherein the water-in-oil emulsion comprises a surfactant with the adjuvanting oil.

18. A vaccine composition according to claim 1, comprising:

a water-in-oil emulsion;

a plurality of alginate particles loaded with particulate immunogens dispersed in the aqueous phase of the water-in-oil emulsion, and chitosan surrounding and complexed with the alginate particles.

19. A vaccine composition according to claim 18, wherein a portion of the immunogen is partitioned within the alginate particles to provide for a persistent dose and a portion of the immunogen is partitioned within the chitosan surrounding with said alginate particles in the form of a continuous shell to provide for an initial priming dose, and wherein the weight ratio of the hydrogel core to the surrounding shell is preferably 1:4 to 4:1 to achieve control of the immunogen release profile across a primary dose and sustain release.

20. A vaccine composition according to claim 18, wherein the water-in-oil emulsion comprises an adjuvant that produces a water-in-oil emulsion or water-in-oil-in-water emulsion.

21. A method of delivering an immunogen to a subject for the treatment or prevention of a disease or disorder in the subject, the method comprising the step of administering the vaccine composition of claim 1 to the subject by injection.

* * * * *